(12) United States Patent
Schenkel et al.

(10) Patent No.: US 7,655,776 B2
(45) Date of Patent: Feb. 2, 2010

(54) BOVINE CAST GENE SNP AND MEAT TENDERNESS

(75) Inventors: Flavio Schramm Schenkel, Guelph (CA); Stephen Paul Miller, Puslinch (CA); Zhihua Jiang, Pullman, WA (US)

(73) Assignee: University of Guelph (CA)

( * ) Notice: Subject to any disclaimer, the term of this patent is extended or adjusted under 35 U.S.C. 154(b) by 310 days.

(21) Appl. No.: 11/183,499

(22) Filed: Jul. 18, 2005

(65) Prior Publication Data

US 2006/0211006 A1 Sep. 21, 2006

Related U.S. Application Data

(60) Provisional application No. 60/662,282, filed on Mar. 16, 2005.

(51) Int. Cl.
C07H 21/02 (2006.01)
C07H 21/04 (2006.01)
C12Q 1/68 (2006.01)
C12P 19/34 (2006.01)

(52) U.S. Cl. .................. 536/23.1; 536/24.3; 536/24.31; 536/24.33; 435/6; 435/91.2

(58) Field of Classification Search ........................ None
See application file for complete search history.

(56) References Cited

U.S. PATENT DOCUMENTS

2001/0053519 A1* 12/2001 Fodor et al. ..................... 435/6
2004/0101842 A1   5/2004 Haley
2005/0065736 A1   3/2005 Bauck

FOREIGN PATENT DOCUMENTS

| WO | WO 9511995 A1 * | 5/1995 |
| WO | WO02064820 A1 | 8/2002 |
| WO | WO03046203 A2 | 6/2003 |
| WO | WO03060151 A2 | 7/2003 |

OTHER PUBLICATIONS

Chung Hy et al ' Relationship of a PCR-SSCP at the bovine calpastatin locus with calpastatin activity and meat tenderness' Special Circular—Ohio Agricultural Research and Development Center (1999) No. 170, printed pp. 1-9 and citation.*
GenBank GI:10946524 (2000) 'Bos taurus calpastatin gene, exon 5 and 6 and partial cds.' LOCUS AY008267, pp. 1-2.*
Ahern, H. 'Biochemical, reagent kits offer scientists good return on investment.' The Scientist (1995) 9(15), pp. 20 and 22.*
GenBank AC004104 (Jun. 13, 1998) "*Homo sapiens* 12q24 PAC RPCI5-942N13 (Roswell Park Cancer Institute Human PAC library) complete sequence" GI:3219327, from www.ncbi.nlm.nih.gov, printed pp. 1-44.*
Chung HY, Davis ME, Hines HC. Genetic variants detected by PCR-RFLP in intron 6 of the bovine calpastatin gene. Anim Genet. Feb. 2001;32(1):53.
Lonergan SM, Ernst CW, Bishop MD, Calkins CR, Koohmaraie M. Relationship of restriction fragment length polymorphisms (RFLP) at the bovine calpastatin locus to calpastatin activity and meat tenderness. J Anim Sci. Dec. 1995;73(12):3608-12.
Green R D et al: Association of a taql calpastatin polymorphism with postmortem measures of beef tenderness in charolais and limousin-sired steers and heifers Journal of, Animal Science, New York, NY, US, vol. 74, No. Suppl. 1, Jan. 1, 1996, p. 113.
Green R D et al: Association of a taql calpastatin polymorphin with postmortem measures of beef tenderness in bos Taurus and bos indicus-bos taurus steers and heifers Journal of Animal Science, New York, NY, US, vol. 74, No. Suppl. 1, Jan. 1, 1996, p. 111.
Schenkel F S et al: Association of a single nucleotide polymorphism in the calpastatin gene with carcass and meat quality traits of beef cattle. Journal or Animal Science Feb. 2006, vol. 84, No. 2, Feb. 2006, pp. 291-299.

* cited by examiner

*Primary Examiner*—Stephen Kapushoc
(74) *Attorney, Agent, or Firm*—Judy Jarecki-Black; Thomas Kowalski, Esq.; Merial Limited

(57) ABSTRACT

The present invention relates to the identification of a single nucleotide polymorphism (SNP) within the bovine CAST locus encoding the calpastatin protein, wherein the allelic variation of the SNP is a G/C transversion associated with post-mortem muscle tenderness. The invention further relates to oligonucleotides useful in identifying the genotype of bovines as it relates to the CAST locus polymorphic site. The invention also encompasses computer-assisted methods and systems for improving the production efficiency for livestock having marketably tender meat using multiple data, and in particular the genotype of the animals as it relates to the CAST SNP. These methods of the invention encompass obtaining a genetic sample from each animal in a herd of livestock, determining the genotype of each animal with respect to specific quality traits as defined by a panel of at least two single polynucleotide polymorphisms (SNPs), one SNP corresponding to a site between exons 5 and 6 of the bovine CAST locus, grouping animals with like genotypes, and optionally, further sub-grouping animals based on like phenotypes.

4 Claims, 4 Drawing Sheets

SEQ ID NO: 1
      FORWARD PRIMER
ATGAGAAAAAAACCCAAGAAGTAAAGCCAAAGGAACACACAGAGGTAAGTAATCATTATTAGGA
CTTGATATCATAAGATGAAGCCTTTTTTTTTTTCCCTTATTTTTGTGAAGGATAAAATTTTGAA
CTCTCATCTTTCAACACTTAAGTCCTACCTAGAATGGCAGTTATTTGTTTTTCTGTTAAAACGG
CACCTCTGTGTGGCATCAGCAGGTATTGCAATTTGCTTGTGTGATTCTTGCTGAATTTGGAAGG
AAGGAATTGCATTGTTTCAAATTTT<u>C</u>TACCCAAAGTGAAATTTGTCACATGTAAATCATACTAA
TTTAAATTCTCACAATTGACTACATAAAACACAAGTGTTATGAATTGCTTTCTACTCCTCAGAG
AAAAGTAGCAATATGTGTCATATTATTAACCCCATGGGGTGTATGCGTGTTTTCAGCCAAAAAG
CCTACCCAAGCACTCATCAGATACAGGAAGCAAGCATGCTCCTAAGGAAAAAGCCGTTTCCAAA
TCAAGTGAGCAGCCACCATCAGAGAAATCAACAAAACCAAAG
 REVERSE PRIMER

*Fig. 1*

Examples of Genotypes for the CAST SNP:

Lane 1 Homozygote CC

Lane 4 Homozygote GG

Lane 9 Heterozygote CG

SEQUENCE LISTING

<160> NUMBER OF SEQ ID NOS: 4

<210> SEQ ID NO 1
<211> LENGTH: 554
<212> TYPE: DNA
<213> ORGANISM: Bos taurus

<400> SEQUENCE: 1

```
atgagaaaaa aacccaagaa gtaaagccaa aggaacacac agaggtaagt aatcattatt      60
aggacttgat atcataagat gaagcctttt tttttttccc ttattttgt gaaggataaa      120 attttgaact ctcatctttc aacacttaag tcctacctag aatggcagtt atttgttttt      180
ctgttaaaac ggcacctctg tgtggcatca gcaggtattg caatttgctt gtgtgattct      240
tgctgaattt ggaaggaagg aattgcattg tttcaaattt tctacccaaa gtgaaatttg      300
tcacatgtaa atcatactaa tttaaattct cacaattgac tacataaaac acaagtgtta      360
tgaattgctt tctactcctc agagaaaagt agcaatatgt gtcatattat taaccccatg      420
gggtgtatgc gtgttttcag ccaaaaagcc tacccaagca ctcatcagat acaggaagca      480
agcatgctcc taaggaaaaa gccgtttcca aatcaagtga gcagccacca tcagagaaat      540
caacaaaacc aaag                                                        554
```

<210> SEQ ID NO 2
<211> LENGTH: 41
<212> TYPE: DNA
<213> ORGANISM: Artificial Sequence
<220> FEATURE:
<223> OTHER INFORMATION: SEQ ID NO: 2 = synthetic 'forward' primer

<400> SEQUENCE: 2

```
cctcgactgc gtaccaattc cgaagtaaag ccaaaggaac a                          41
```

<210> SEQ ID NO 3
<211> LENGTH: 25
<212> TYPE: DNA
<213> ORGANISM: Artificial Sequence
<220> FEATURE:
<223> OTHER INFORMATION: SEQ ID NO: 3 = synthetic 'reverse' primer

<400> SEQUENCE: 3

```
atttctctga tggtggctgc tcact                                            25
```

<210> SEQ ID NO 4
<211> LENGTH: 21
<212> TYPE: DNA
<213> ORGANISM: Artificial Sequence -continued

```
<220> FEATURE:
<223> OTHER INFORMATION: SEQ ID NO: 4 = synthetic primer

<400> SEQUENCE: 4
cctcgactgc gtaccaattc c                                              21
```

BOVINE CAST GENE SNP AND MEAT TENDERNESS

INCORPORATED BY REFERENCE

This Application claims priority to U.S. Provisional Application Ser. No. 60/662,282 titled "Association of a Single Nucleotide Polymorphism in the Calpastatin (CAST) Gene with Carcass and Meat Quality Traits of Beef Cattle" filed Mar. 16, 2005. All documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of a single nucleotide polymorphism (SNP) within the bovine gene encoding calpastatin and its association with carcass and meat quality. The invention further relates to methods and systems, such as network-based processes, to manage the calpastatin and other SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Meat tenderness is an important issue in production of beef cattle, because it has a major impact on consumer's satisfaction. Consumers consider tenderness to be the single most important component of meat quality (Miller, (1992) Beef Today 8:40). The physiological change in muscle structure leading to increased tenderness during the postmortem period is complex (Koohmaraie, M. (1994) Meat Sci. 36: 93). The calpain/calpastatin system is an endogenous, calcium-dependent proteinase system, theorized to mediate the proteolysis of key myofibrillar proteins during postmortem storage of carcass and cuts of meat at refrigerated temperatures. Calpain is involved in the breakdown of myofibril protein, which is closely related to meat tenderness (Wheeler and Koohmaraie, 1994). Calpastatin inhibits µ- and m-calpain activity and, therefore, regulates postmortem proteolysis in part.

Many known non-genetic sources of variation may affect postmortem meat tenderization, including, for instance, the age of the cattle, deeding management, degree of stress prior to slaughter, and postmortem aging time (Tatum et al. 2000). However, approximately 30% of the variation in tenderness of meat can be explained by additive gene effects within a single breed (Koch et al. (1982) J. Anim. Sci. 1319-1329), which is greater than variation found among breeds (Wheeler et al. (1996) J. Anim. Sci. 74: 1023-1035).

An increase in postmortem calpastatin activity has been correlated to reduced meat tenderness (e.g., Koohmaraie et al. 1995 in: Ouali et al. (eds.) Expression of Muscle Proteinases and Regulation of Protein Degradation as Related to Meat Quality. Audet Tijdschrifren b.v., Nijmegen, The Netherlands pp 395-412; Pingle et al. 1997). The calpastatin (CAST) gene, mapped to bovine chromosome 7 (Bishop et al., J Anim Sci. 1993 August; 71(8):2277), is considered a candidate gene for beef tenderness. Initial studies, however, did not find significant association of CAST polymorphisms with tenderness. For instance, Lonergan et al. (1995) (J. Anim. Sci. 73: 3608-3612) did not find a significant association of restriction fragment length polymorphisms in the CAST gene with calpastatin activity or tenderness in crossbred offspring of sires from eight breeds. Chung et al. (1999) (J. Anim. Sci. 77 (Suppl 1): 31) investigated the association of PCR single strand conformation polymorphisms in the CAST gene with calapastatin activity, Warner-Bratzler shear force and myofibril fragmentation index in forty-seven purebred Angus bulls and concluded that the polymorphisms were not useful for prediction of calpastatin activity, myofibril fragmentation index or meat tenderness.

More recently two genetic tests for meat tenderness in beef have become available. The TenderGENE™ test (Merial Limited) is based on two markers (polymorphisms) in the Calpain gene. The GeneStar® Tenderness 2 (Genetic Solutions) is based on a marker in the CAST gene and one marker in the Calpain gene.

"Body condition" as understood in the livestock industry is the state of development of an animal as a function of frame type or size, and overall health and, in the case of non-poultry animals, the amount of intramuscular fat and back fat exhibited by an animal. The body condition of animals is a determinant of market readiness in commercial livestock breeding, feeding and finishing operations. Body condition is typically determined subjectively and through experienced visual appraisal of live animals. The fat deposition, or the amount of intramuscular fat and back fat on a non-poultry animal carcass, is important to industry participants because carcasses exhibiting desired amounts and proportions of such fats can often be sold for higher prices than carcasses that exhibit different amounts and proportions of fat. Furthermore, the desired carcass fat deposition often varies among different markets and buyers with time within single markets and among particular buyers in response to public demand trends with respect to desired fat and marbling in meats. Predictable and consistent body weight or carcass characteristics are also preferred.

Presently, cattle entering a feedlot are divided into groups according to estimated age, frame size, breed, weight, and so forth. By making such a division, the feedlot owner is attempting to group the animals so that a group can be penned together, fed the same diet and slaughtered at the same time. Weight and visual cues are one means possible to sort cattle for feedlot grouping.

The greater the production expectations, the greater the price realized by the feed operator. Regardless of the particular market preference at a given time, the feed lot operator will be trying to tailor his animals to meet some similar standard that will cause a meat packer or commercial purchaser to pay the highest price in accordance with currently prevailing market preferences.

While the cost of acquiring each animal in a group can vary somewhat, the feedlot operator's costs would be the same for each animal in a group since they would have access to the same amount of feed and occupy space in the feedlot for the same amount of time (not considering health costs due to sickness). Thus, the price reductions for animals falling outside the desirable range fall directly to the feedlot operator's bottom line, resulting in reduced profits. One way to reduce costs and increase profits is to minimize the time an animal spends at the feedlot, thereby reducing feed costs. Thus, longer residence times are usually only profitable if the result is an animal with a more profitable grade. The capability of predicting when an animal is ready for a market is also desirable.

There remains a need for methods that allow relatively easy and more efficient selection and breeding of farm animals with an advantage for an inheritable trait of growth rate, body weight, carcass merit, feed intake and milk yield and composition. The economic benefits of the use of genetic markers that are associated with specific economically important traits (especially traits with low heritability) in livestock through marker-assisted selection are significant.

Polymorphisms in the coding regions of the leptin gene in cattle have been associated with milk yield and composition (Liefers et al. (2002) J. Dairy Sci. 85: 1633-1638; Buchanan et al (2003) Dairy Sci. 86: 3164-3166), feed intake (Liefers et al. (2002); Lagonigro et al. (2003) Anim. Genet. 34: 371-374), and body fat (Buchanan et al. (2002) Genet. Sel Evol. 34: 105-116; Lagonigro et al., Anim Genet. 2003 October; 34(5):371-4. However, polymorphisms located in the promoter region of the leptin gene (i.e. the region of the gene that regulates the level of leptin expression through its associated enhancer and silencer elements) may have a stronger effect on the regulation of these economically important traits, and therefore be of greater predictive value.

Other SNPs identified with phenotypes of interest to the animal breeder or rearer are, for example, within the m-calpain (CAPN1) gene (Juszczuk-Kubiak et al. (2004) J. Appl. Genet. 45: 457-460. An SNP in the DGAT1 gene affects milk yield and composition (Grisar et al. (2004) Proc. Natl. Acad. Sci. U.S.A. 101: 2398-2403; Thaller et al. (2003) Anim. Genet. 34: 354-357; Kuhn et al. (2004) Genetics 167: 1873-1881). SNPs in the growth hormone receptor gene GHR may have significant effects on milk yield in particular breeds of cattle (Spelman et al. (2002) J. Dairy Sci. 85: 3514-3517; Blott et al. (2003) Genetics 163: 253-266).

Because of these deficiencies and others inherent in the prior art, it is still advantageous to provide further SNPs that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of a single nucleotide polymorphism (SNP) within the bovine CAST locus encoding the calpastatin protein and in one embodiment, the allelic variation of the SNP is a G/C transversion associated with post-mortem muscle tenderness. The invention further relates to oligonucleotides useful in identifying the genotype of bovines as it relates to the CAST locus polymorphic site. The invention, therefore, also encompasses computer-assisted methods and systems for improving the production efficiency for livestock having marketable tender meat using multiple data, and in particular the genotype of the animals as it relates to a CAST SNP. Methods of the invention encompass obtaining a genetic sample from each animal in a herd of livestock, determining the genotype of each animal with respect to specific quality traits as defined by a panel of at least two single polynucleotide polymorphisms (SNPs), one SNP corresponding to a site located between exons 5 and 6 of the bovine CAST locus, grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip or radiofrequency tag. An advantageous aspect of the present invention, therefore, is directed to a computer system and computer-assisted methods for tracking quality traits of livestock possessing specific genetic predispositions.

The present invention advantageously encompasses computer-assisted methods and systems for acquiring genetic data, particularly genetic data as defined by the absence or presence of a SNP within the calpastatin gene related to meat quality traits of the breed of animal and associating that data with other data about the animal or its herd, and maintaining that data in ways that are accessible.

In one embodiment, alleles of the CAST SNP identified by present invention segregate in the beef population with overall higher frequency for allele C than G. Allele C is associated with improvements in muscle tenderness across post-mortem aging days, but tends to reduce Longissimus muscle area and lean yield, while increasing fat yield. Importantly for the beef industry, the difference in the tenderness is predicted to substantially reduce the percentage of carcasses rated unacceptably tough by consumers. Homozygous CC and heterozygous CG cattle may produce more tender carcasses, which may result in improved organoleptic properties. More tender carcasses can produce better, more tasty meat (e.g. more flavorful better mouthfeel), thereby leading to better meals.

One aspect of the invention, therefore, encompasses isolated nucleic acid molecules that encompass a polymorphic nucleotide other than cytosine that when subject to a G/C transversion generates an Rsa I restriction endonuclease site. Various embodiments of the invention encompass oligonucleotides that may selectively hybridize under high stringency conditions to any nucleotide sequence between exons 5 and 6 of the CAST gene, or any complement thereof.

This aspect, therefore, of the invention encompasses isolated nucleic acid molecules that may have a polymorphic Rsa I restriction site and which may selectively hybridize under high stringency conditions to a nucleotide sequence according to SEQ ID NO: 1 or the complement thereof, wherein the polymorphic site is nucleotide position 282 of SEQ ID NO: 1, and wherein the polymorphic nucleotide is guanine.

One embodiment of this aspect of the invention provides an oligonucleotide that hybridizes to a portion of the isolated nucleic acid molecule of this aspect of the invention and may include the polymorphic site at nucleotide position 282 of SEQ ID NO: 1.

Other embodiments of the invention encompass oligonucleotides that hybridize under high stringency conditions to the polymorphic site of the bovine CAST gene and corresponding to nucleotide position 282 of SEQ ID NO: 1, and wherein the oligonucleotide is between about 18 nucleotides and about 50 nucleotides.

In another embodiment of the invention, the oligonucleotide may comprise a central nucleotide specifically hybridizing with a CAST gene polymorphic site of the portion of the nucleic acid molecule, and wherein said nucleic acid molecule may comprise a cytosine or guanine corresponding to the nucleotide position 282 of the sequence SEQ ID NO: 1.

In other embodiments of the invention, the oligonucleotide may comprise a nucleotide sequence which may hybridize under high stringency conditions to oligonucleotides which may comprise sequences according to SEQ ID NOS: 2 and 3.

Other embodiments of the present invention encompass isolated nucleic acids generated by the amplification of a region of bovine genomic nucleic acid, wherein the amplification encompasses obtaining a sample of genetic material from a bovine individual, and amplifying a region of the isolated genetic material which may comprise a single nucleotide polymorphic site corresponding to nucleotide position 282 of sequence SEQ ID NO: 1 using oligonucleotide primers that may encompass sequences according to SEQ ID NOS: 2 and 3.

Another aspect of the invention is a method of identifying a calpastatin polymorphism in a nucleic acid sample which may comprise isolating a nucleic acid molecule encoding calpastatin or a fragment thereof and determining the nucleotide at the polymorphic site corresponding to nucleotide position 282 of SEQ ID NO: 1.

In one embodiment of the methods of this aspect of the invention, the polymorphism may be identified by cleavage of the nucleic acid sample by Rsa I restriction enzyme. In other embodiments, the nucleic acid sample may be obtained from a plurality of bovines and the nucleotide occupying the polymorphic sites may be determined in each of the bovines and wherein the method may further comprise testing each bovine for the presence of a meat quality phenotype and correlating the meat quality phenotype with the nucleotide occupying the polymorphic site. In these embodiments of the invention, the meat quality phenotype may be defined by at least one trait, such as but not limited to, percentage of lean (LEANYL), fat (FATYL) and bone (BONEYL) yields, grade fat (GFAT), Longissimus muscle (LM) area (LMA), hot carcass weight (HCW), chemical fat (CF) or intramuscular fat content, quality grade (QG) or marbling, tenderness by taste panel, and tenderness (shear force or other instrumental measures) of LM at 2 (SFL2), 7 (SFL7), 14 (SFL14) and 21 (SFL21) days post-mortem and of Semitendinosus muscle at 7 (SFS7) days post-mortem.

In various embodiments of the invention, the method may further comprise the step of amplifying a region of the calpastatin gene or a portion thereof that contains a polymorphism. In other embodiments of the invention, the amplification may include the step of selecting a forward and a reverse sequence primer which may amplify a region of the calpastatin gene according to SEQ ID NO: 1, wherein the amplified region may comprise a polymorphic nucleotide corresponding to nucleotide position 282 of sequence SEQ ID NO: 1.

Another aspect of the invention encompasses a method of screening cattle to determine those bovines more likely to exhibit a biological difference in meat quality which may comprise the steps of obtaining a sample of genetic material from a bovine; and assaying for the presence of a genotype in the bovine which is associated with meat quality, the genotype may be characterized by a G/C transversion polymorphism in the calpastatin gene, wherein the polymorphism may be located at nucleotide position 282 of the sequence SEQ ID NO: 1. In the various embodiments of this aspect of the invention, the polymorphism may be advantageously identified by an Rsa I restriction enzyme.

In other embodiments of this aspect of the invention, the step of assaying may be selected from the group consisting of restriction fragment length polymorphism (RFLP) analysis, minisequencing, MALDI-TOF, bi-directional PCR amplification of specific allele (Bi-PASA), heteroduplex analysis, single strand conformational polymorphism (SSCP), double-stand conformation polymorphisms (DSCP), denaturing gradient gel electrophoresis (DGGE) and temperature gradient gel electrophoresis (TGGE).

In various embodiments of the invention, the method may further encompass the step of amplifying a region of the calpastatin gene or a portion thereof that contains the polymorphism. In some embodiments of the invention, the amplification may include the step of selecting a forward and a reverse sequence primer which amplifies a region of the calpastatin gene, such as SEQ ID NO: 1, and the amplified region may include a polymorphic Rsa I restriction site at nucleotide position 282 of SEQ ID NO: 1.

In the embodiments of the invention, the forward and reverse amplification primers may be SEQ ID NOS: 2 and 3 or any other forward and reverse primers that spans intron 5 of the CAST gene locus.

Another aspect of the invention encompasses a computer-assisted method for predicting which livestock animals possess a biological difference in meat quality, and which may include the steps of using a computer system, e.g., a programmed computer comprising a processor, a data storage system, an input device and an output device, the steps of: (a) inputting into the programmed computer through the input device data that includes a calpastatin genotype of an animal as it relates to a SNP in the CAST gene locus, (b) correlating meat quality predicted by the calpastatin genotype using the processor and the data storage system and (c) outputting to the output device the meat quality correlated to the calpastatin genotype, thereby predicting which livestock animals possess a particular meat quality. In an advantageous embodiment, SNP is located in intron 5 of the CAST gene.

Yet another aspect of the invention relates to a method of doing business for managing livestock comprising providing to a user a computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic is meat quality, advantageously to meat tenderness, and a genotype is a calpastatin genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 1 illustrates the nucleotide sequence SEQ ID NO: 1 of a region of the bovine calpaststin CAST gene locus that includes intron 5 thereof (Genbank Accession No. AY008267).

DETAILED DESCRIPTION

Figure 2:
FIG. 2 illustrates Rsa I restriction digest patterns of PCR amplified products from several bovine individuals bearing nucleotide polymorphisms within the CAST gene.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphisms sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Because these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβBRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-standard DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the MRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides liked by a phosphodiester backbone. A "modified polynucleotide" refers to a polynucleotide in which one or more natural nucleotides have been partially or substantially completely replaced with modified nucleotides.

A "primer" is an oligonucleotide, the sequence of at least a portion of which is complementary to a segment of a template DNA which is to be amplified or replicated. Typically, primers are used in performing the polymerase chain reaction (PCR). A primer hybridizes with (or "anneals" to) the template DNA and is used by the polymerase enzyme as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) *Science* 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs. Wherein the gene of interest is bovine calpastatin, the bovine calpastatin nucleotide sequence can be selected from, but is not limited to, any one of the sequences corresponding to GenBank Accession Nos. AF159246 (Cong et al. (1998) J. Biol. Chem. 273: 660-666); L14450 (Killefer & Koohmaraie (1994) J. Anim. Sci. 72: 606-614); NM_174003 (Cummins et al. (2004) J. Dairy Sci. 87: 1428-1431); and X67333 (Parr et al. (1992) Eur. J. Biochem. 208: 333339, or a fragment thereof.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. Of course, it is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

Traits relating to meat quality and tenderness may be grouped into two groups: (i) carcass yield traits: percentage of lean (LEANYL), fat (FATYL) and bone (BONEYL) yields, grade fat (GFAT), Longissimus muscle (LM) area (LMA), and hot carcass weight (HCW) and (ii) meat quality traits: chemical fat (CF) or intramuscular fat content, quality grade (QG) or marbling, tenderness by taste panel, and tenderness (shear force or other instrumental measures) of LM at 2

(SFL2), 7 (SFL7), 14 (SFL14) and 21 (SFL21) days postmortem and of Semitendinosus muscle at 7 (SFS7) days post-mortem.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality and quantity of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine calpastatin, the bovine calpastatin nucleotide sequence can be selected from, but is not limited to, the sequence corresponding to GenBank Accession No. AY0008267 (Chung et al. (2001) Animal Genetics 32: 53) or a fragment thereof or a region of the bovine genome that comprises this sequence.

The present invention, therefore, provides isolated nucleic acids that may specifically hybridize to the nucleotide sequence SEQ ID NO: 1 corresponding to GenBank Accession No. AY0008267, or a complement thereof, and which comprises the polymorphic site corresponding to nucleotide position 282 of SEQ ID NO: 1 located between exons 5 and 6 of the calpaststin CAST gene locus. One allelic variant of this polymorphic site is a guanine (G) nucleotide that is associated with decreased meat tenderness and quality. The alternative allelic form has a cytosine (C) nucleotide in this position and is conversely associated with enhanced meat tenderness. Thus, animals CC homozygous have the most tender meat and GG homozygotes have the least tender meat. CG heterozygotes for the SNP which is the subject of the invention have an intermediate level of meat tenderness.

The advantageous SNP in the present invention is associated with certain economically valuable heritable traits relating to meat quality in bovines. Therefore, it is an object of the present invention to determine the genotype of a given animal of interest as defined by the calpastatin (CAST) locus SNP according to the present invention. It is also contemplated that the genotype of the animal(s) may be defined by additional SNPs within the calpastatin gene or within other genes identified with desirable traits or other characteristics, and in particular by a panel or panels of SNPs. The association of calpastatin SNP according to the invention herein with various economically significant traits are shown in Examples 5-8 below.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits relating to meat quality, most advantageously to meat tenderness, to be identified based on the presence of single nucleotide polymorphisms (SNP) in their genomes and particularly with an SNP located between exons 5 and 6 of the CAST (calpastatin) gene. The methods further allow, by computer-assisted methods of the invention, to correlate the SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of the CAST (calpastatin) gene of the present invention may be determined by sequencing the region of the genomic DNA sample that spans the polymorphic locus. Many methods of sequencing genomic DNA are known in the art, and any such method can be used, see for example Sambrook et al. Molecular Cloning; A Laboratory Manual 2d ed. (1989). For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the Calpastatin gene, advantageously of the region encompassing the SNP located between exons 5 and 6 of the bovine CAST gene locus. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. Exemplary primer sequences for use in the invention include, but are not limited to, 5'-CCTCGACT-GCGTACCAATTCCGAAGTAAAGCCAAAGGAACA-3' (SEQ ID NO: 2) (forward) and 5'-ATTTCTCTGATGGTG-GCTGCTCACT-3'(SEQ ID NO: 3). The first 21 nucleotides at the 5'extreme of the primer SEQ ID NO: 2 are a tag region that may be useful in the sequencing of PCR products, but are not found within the CAST gene sequence itself.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3$H, $^{125}$I, $^{35}$S, $^{14}$C, $^{32}$P, etc. Well-known labeling methods are described, for example, in Sambrook et al. Molecular Cloning; A Laboratory Manual 2d ed. (1989). The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing C or G as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic calpastatin (CAST) locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mis-matched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises an SNP such as the Rsa I SNP of the CAST locus according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified. When designing primers for amplification of the CAST gene polymorphism, one primer should be located upstream of the nucleotide position corresponding to nucleotide position 282 of the sequence SEQ ID NO: 1, and the other primer must be located downstream of, but not including, the nucleotide position corresponding to nucleotide position 282 of the sequence SEQ ID NO: 1. For example, a fragment of DNA spanning the location of the CAST polymorphism can be amplified from a nucleic acid sample using a forward primer with the sequence 5'-CCTC-GACTGCGTACCAATTCCGAAGTAAAGC-CAAAGGAACA-3' (SEQ ID NO: 2), and reverse primer with the sequence 5'-ATTTCTCTGATGGTGGCTGCT-CACT-3' (SEQ ID NO: 3).

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^{3}H$, $^{125}I$, $^{35}S$, $^{14}C$, $^{32}P$, etc.), enzymes (e.g. horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. Molecular Cloning; A Laboratory Manual 2d ed. (1989). For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Georgia) or SeqWright DNA Technologies Services (Houston, Texas).

An SNP-specific probe can also be used in the detection of the SNP in amplified specific nucleic acid sequences of the target CAST gene, such as the amplified PCR products generated using the primers described above. In certain embodiments, these CAST SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer SEQ ID NO: 2 that may provide a site to which an oligonucleotide sequencing primer may hybridize to facilitate the sequencing of multiple PCR samples.

The probe sequence must span the particular nucleotide position that may be substituted in the particular SNP to be detected. For example, probes designed for detection of the Rsa I polymorphism located between exons 5 and 6 of the CAST gene locus must span the nucleotide position that corresponds to nucleotide position 282 of the sequence SEQ ID NO: 1.

Advantageously, two or more different "allele-specific probes" may be used for analysis of a SNP, a first allele-specific probe for detection of one allele, and a second allele-specific probe for the detection of the alternative allele. For example, in one embodiment the different alleles (C,G) of the CAST calpastatin polymorphism can be detected using two different allele-specific probes, one for detecting the G-containing allele at nucleotide position 282 of the CAST gene sequence SEQ ID NO: 1, and another for detecting the C-containing allele at nucleotide position 282 of the CAST gene sequence SEQ ID NO: 1. In a preferred embodiment, an oligonucleotide probe is used to specifically detect the G-containing allele, and another oligonucleotide probe is used to detect the C-containing allele.

It will be understood that this invention is not limited to the particular primers and probes disclosed herein and is intended to encompass at least nucleic acid sequences that are hybridizable to the calpastatin sequence according to SEQ ID NO: 1, the complement or a fragment thereof, or are functional sequence analogs of these sequences. It is also contemplated that a particular trait of an animal may be determined by using a panel of SNPs associated with that trait. As shown in Examples 5-8 below, several economically important phenotypic traits related to meat quality, including tenderness, may be characterized by the presence or absence of one or more SNPs including the CAST SNP, and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for the desirable C allele of the CAST gene polymorphic site associated with improved carcass merit, would lead to a breed, line, or population having higher numbers of offspring with improved carcass merit. Thus, the calpastatin SNP of the present invention can be used as a selection tool.

Using the methods of the present invention, such as by determining the Rsa I restriction digest pattern of the PCR products, as described in Example 9 below, one can determine whether a given animal has a cytosine or a guanine at the polymorphic site located at nucleotide position 282 of the sequence according to SEQ ID NO: 1 and whether the bovine individual is homozygous or heterozygous for this SNP. Having used the methods of the invention to determine the genotype of an animal of interest as having, for example, the GG, GC or CC genotype of the CAST calpaststin gene, it is a further object of the present invention to utilize this genotype information to select and/or group animals according to their genotype and to enter this data into a computer system of the invention.

The C allele of the CAST calpaststin gene SNP is associated with certain economically important traits, in particular traits associated with meat quality and most especially meat tenderness. Alleles of the identified CAST SNP segregate in the beef population with an overall higher frequency for the C allele than the G allele with exception of Simmental animals that conversely showed a higher incidence of G allele.

The C allele is associated with significant improvements in Longissimus muscle (LM) tenderness across postmortem aging days and tended to indicate improvements in the tenderness of semitendinous (ST) muscle. The magnitude of the effect of the C allele was similar to that one reported for the GeneSTAR® tender allele. The polymorphism in the CAST gene (Barendse, 2002) used in the GeneSTAR® test is, however, different from the SNP at nucleotide position 282 of the sequence according to SEQ ID NO: 1.

The difference in LM shear force between homozygote genotypes CC and GG was equivalent to half (53%) of the estimated effect of 7 days of aging on LM tenderization obtained from the data by linear regression of LM shear force on days postmortem. Deviations from the linear curve were not significant. The favorable effect of the C allele on tenderness significantly decreased the expected percentage of unacceptable steaks (shear force >5.7 kg) at 7 days postmortem (decreased by 27% and 39% for cattle carrying 1 or 2 copies of the C allele compared to those animals with no copies of the C allele). Above the threshold of 5.7 kg of peak shear force, 100% of the consumers typically would rate a steak as unacceptably tough.

Koohmaraie et al. (1997) in: Ouali et al. (eds.) Expression of Muscle Proteinases and Regulation of Protein Degradation as Related to Meat Quality. Audet Tijdschrifren b.v., Nijmegen, The Netherlands pp 395-412 stated that to improve the consistency of meat quality with respect to tenderness, beef should be aged at least 14 days. Considering 14 days of aging, the estimated percentage of unacceptable meat quality (as assessed by meat tenderness) decreased by 35% (from 20.4% to 13.2%) and by 42% (from 20.4% to 11.8%) for cattle carrying 1 or 2 copies respectively of the C allele compared to cattle carrying no C allele. The rate of tenderization as the meat aged was not affected by the CAST SNP genotypes showing that the genotypes with more tender LM at 2 days postmortem may also have more tender beef in subsequent days postmortem.

The amount of phenotypic variance explained by the CAST polymorphism varied from 0.4 to 1.6% for the different postmortem days. The genotypic variance associated with the CAST polymorphism was estimated by standard formulae provided by Falconer and Mackay (1996). Despite the small contribution to the phenotypic variation, the CAST genotypic effects were large enough to substantially decrease the expected percentage of tough steaks. In a bi-allelic locus, gene effects (additive and dominance) must be large to account for substantial phenotypic variance of quantitative traits. The C allele was, therefore favorable for LM tenderness, but the same allele tended to reduce LM area and lean yield, while significantly increasing fat yield.

The present invention, therefore, provides a SNP wherein the C allele of the CAST locus is significantly associated with meat tenderness, being lowest in homozygous animals with the GG genotype, intermediate in heterozygous animals with the CG genotype, and highest in homozygous CC animals. While it is desirable to group animals according to meat quality or tenderness (for example for use in food production or for breeding), animals can be selected and grouped according to their genotype at the polymorphic CAST calpastatin SNP corresponding to the nucleotide position 282 of the sequence SEQ ID NO: 1.

One aspect of the present invention provides for grouping animals and methods for managing livestock production comprising grouping livestock animals such as cattle according the genotype as defined by panels of SNPs, each panel comprising at least one SNP, one of which is the CAST calspastatin SNP corresponding to the nucleotide position 282 of the sequence SEQ ID NO: 1. Other SNPs that may be included in panels of SNPs include, but not limited to, UASMS1, UASMS2, UASMS3 and/or EXON2-FB SNPs of the ob loci defining the same phenotypic character. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, food consumption, carcass/meat quality and milk production. The present invention provides methods of screening livestock to determine those more likely to develop a desired body condition by identifying the presence or absence of a polymorphism in the CAST calpastatin genes that is correlated with that of meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feed lot operator, or the like, can group cattle according to each animal's genetic propensity for a desired trait such as growth rate, feed intake or feeding behavior, as determined by SNP genotype, in addition to the criteria of meat quality and tenderness as determined by the CAST SNP corresponding to the nucleotide position 282 of the sequence SEQ ID NO: 1 ordinarily used for grouping. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feed lot operator, and then slaughtered.

Thus, a feeder is presented with opportunities for considerable efficiencies. At present, for example, the feeder may feed his cattle in the same manner, incurring the same costs for each animal, and typically, with excellent management practices, perhaps 40% will grade AAA and receive the premium price for the palatability grade depending on several other factors, such as age of animal, because cattle between 17-24 months of age have increased marbling compared to their younger counterparts. Approximately 55% of cattle are slaughtered at an age under 16 months, and 45% would be slaughtered at an age over 17 months. Of these, a significant number will have excess fat and will thus receive a reduced yield grade. The balance of the cattle, 60%, will grade less than AAA, and thus receive a reduced price, although the feedlot costs incurred by the operator will be the same. Grouping and feeding the cattle by CAST genotype, as well as by other factors such as the overall welfare profile, which includes husbandry and veterinary data, allows the feeder to treat each group differently with a view to increasing profit by maximizing, for example, the number of cattle providing marketable tender meat.

The individual genotypic data derived from a panel or panels of SNPs, including the CAST SNP corresponding to the nucleotide position 282 of the sequence SEQ ID NO: 1, of each animal or a herd or flock of animals can be recorded and associated with various other data of the animal, e.g. health information, parentage, husbandry conditions, vaccination history, herd or flock records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, breeding goals, production targets, vaccination levels of a flock or herd. If the performance or properties of the animals deviates from the desired goals, the computer-based methods may trigger an alert to allow the operator to adjust vaccination doses, medications, feed etc accordingly.

The results of the analysis provide data that is associated with the individual animal or to the herd in whole or in part from which the sample was taken. The data is then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd or flock, health information including vaccinations, exposure to diseases, feed lot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dams, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and cards or vials (collectors) useful for collecting samples from which genetic data may be obtained. The collectors are packaged in a container that is encoded with identifying indicia. Advantageously, the packaging is encoded with a bar code label. The collectors are encoded with the same identifying indicia, advantageously with a matching bar code label. Optionally, the packaging contains means for sending the collectors to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the vials and the packaging. Upon shipment of the sampling equipment in fulfillment of the order, the identifying indicia are recorded in a database. Advantageously, the identifier is a bar code label which is scanned when the vials are sent. When the vials are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, SUREHEALTH pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two SNPs that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. This data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication (e.g., presentation such as a computer presentation (e.g., POWERPOINT), internet and email), documentary communication such as computer programs (e.g., WORD), and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted to a feedstock site when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd or flock data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, bovine spongiform encephalopathy (BSE) diagnosis, brucellosis vaccination, FMD (foot and mouth disease) vaccination, BVD (bovine viral diarrhea) vaccination, SUREHEALTH pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary etc history of an animal, correlating the breeding, veterinary etc histories using the processor and the data storage system, outputting to the output device the physical characteristic correlated to the genotype and feeding the animal a diet based upon the physical characteristic, thereby optimizing efficiency of feedlots for livestock.

The invention further comprehends methods of doing business by providing access to such computer readable media and/or computer systems and/or data collected from animals to users e.g., the media and/or sequence data can be accessible to a user, for instance on a subscription basis, via the internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of the CAST gene, and in particular for a SNP at the site corresponding to the nucleotide position 282 of the sequence SEQ ID NO: 1, wherein the kits may comprise at least one oligonucleotide selectively hybridizing to a nucleic acid comprising the sequence according to SEQ ID NO: 1 and instructions for using the oligonucleotide to detect variation in the nucleotide corresponding to the nucleotide position 282 of the sequence SEQ ID NO: 1 of the isolated nucleic acid.

One aspect, therefore, of the invention relates to an isolated nucleic acid molecule comprising a polymorphic Rsa I restriction site and selectively hybridizing under high stringency conditions to a nucleotide sequence according to SEQ ID NO: 1 or the complement thereof, wherein the polymorphic site is nucleotide position 282 of SEQ ID NO: 1, and wherein the polymorphic nucleotide is guanine.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising the polymorphic site at nucleotide position 282 of SEQ ID NO: 1 and which is occupied by a nucleotide other than cytosine.

Another embodiment of the invention is an oligonucleotide that specifically hybridizes under high stringency conditions to a polymorphic site of the bovine CAST gene encoding calpastatin, wherein the polymorphic site is nucleotide position 282 of SEQ ID NO: 1, and wherein the oligonucleotide is between about 18 nucleotides and about 50 nucleotides.

In another embodiment of the invention, the oligonucleotide comprises a central nucleotide specifically hybridizing with a CAST gene polymorphic site of the portion of the nucleic acid molecule, and wherein said nucleic acid molecule comprises a cytosine corresponding to the nucleotide position 282 of the sequence SEQ ID NO: 1.

In other embodiments of the invention, the oligonucleotide comprises a nucleotide sequence selectively hybridizing under high stringency conditions to oligonucleotides comprising sequences according to SEQ ID NOS: 2 and 3.

In other embodiments of the present invention, an isolated nucleic acid comprising a polymorphic Rsa I restriction site of the bovine CAST gene locus and selectively hybridizing under high stringency conditions to a nucleotide sequence according to SEQ ID NO: 1 or the complement thereof, wherein the polymorphic site is nucleotide position 282 of SEQ ID NO: 1 is generated by the amplification of a region of the isolated nucleic acid, wherein the amplification comprises the steps of obtaining a sample of genetic material from a bovine individual, and amplifying a region of the isolated genetic material comprising the single nucleotide polymorphic site corresponding to nucleotide position 282 of sequence SEQ ID NO: 1 using oligonucleotide primers comprising sequences according to SEQ ID NOS: 2 and 3.

Another aspect of the invention is a method of identifying a calpastatin polymorphism in a nucleic acid sample comprising isolating a nucleic acid molecule encoding calpastatin or a fragment thereof and determining the nucleotide at the polymorphic site corresponding to nucleotide position 282 of SEQ ID NO: 1.

In one embodiment of the methods of this aspect of the invention, the polymorphism may be identified by cleavage of the nucleic acid sample by Rsa I restriction enzyme. In other embodiments, the nucleic acid sample may be obtained from a plurality of bovine individuals, and the nucleotide occupying the polymorphic sites may be determined in each of the bovine individuals, and wherein the method further comprises testing each bovine individual for the presence of a meat quality phenotype and correlating the meat quality phenotype with the nucleotide occupying the polymorphic site. In these embodiments of the invention, the meat quality phenotype may be defined by at least one trait selected from percentage of lean (LEANYL), fat (FATYL) and bone (BONEYL) yields, grade fat (GFAT), Longissimus muscle (LM) area (LMA), and hot carcass weight (HCW) and meat quality traits (chemical fat (CF) or intramuscular fat content, quality grade (QG) or marbling, tenderness by taste panel, and tenderness (shear force or other instrumental measures) of LM at 2 (SFL2), 7 (SFL7), 14 (SFL14) and 21 (SFL21) days postmortem and of Semitendinosus muscle at 7 (SFS7) days post-mortem.

Another aspect of the invention is a method of screening cattle to determine those bovine individuals more likely to exhibit a biological difference in meat quality comprising the steps of obtaining a sample of genetic material from a bovine individual; and assaying for the presence of a genotype in the bovine individual which is associated with meat quality, the genotype characterized by a G/C transversion polymorphism in the calpastatin gene, wherein the polymorphism corresponds to the nucleotide position 282 of the sequence SEQ ID NO: 1.

In an embodiment of this aspect of the invention, the polymorphism is identifiable by an Rsa I restriction enzyme. In various embodiments of the invention, the genotype is a Rsa I polymorphism in the calpastatin gene.

In other embodiments of this aspect of the invention, the step of assaying is selected from the group consisting of: restriction fragment length polymorphism (RFLP) analysis, minisequencing, MALDI-TOF, SINE, heteroduplex analysis, single strand conformational polymorphism (SSCP), denaturing gradient gel electrophoresis (DGGE), and temperature gradient gel electrophoresis (TGGE).

In various embodiments of the invention, the method may further comprise the step of amplifying a region of the calpastatin gene or a portion thereof that contains the polymorphism. In other embodiments of the invention, the amplification may include the step of selecting a forward and a reverse sequence primer capable of amplifying a region of the calpastatin gene according to SEQ ID NO: 1, the amplified region comprising a polymorphic nucleotide corresponding to nucleotide position 282 of sequence SEQ ID NO: 1.

In the embodiments of the invention, the forward and reverse primers may be according to SEQ ID NOS: 2 and 3 respectively.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising a calpastatin genotype of an animal, (b) correlating meat quality predicted by the calpastatin genotype using the processor and the data storage system and (c) outputting to the output device the meat quality correlated to the calpastatin genotype, thereby predicting which livestock animals possess a particular meat quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic is meat quality and a genotype is a calpastatin genotype.

It should be understood that the present invention is not limited to the specific compositions, equipment or methods described herein and that any method steps equivalent to those described falls within the scope of the present invention. The method steps for determining the profile of an animal are merely exemplary so as to enable one of ordinary skill in the art to use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention is further described by the following non-limiting examples:

EXAMPLES

Example 1

Experimental Cattle and DNA Isolation

A total of 628 animals were genotyped, including commercially fed heifers (163), steers (226) and bulls (61) from beef feedlots in Ontario, and steers (178) from a University of Guelph feeding trial in Rockwood, Ontario. The two sources of cattle were identified as Commercial and Rockwood, respectively. Animals were crossbred with breed composition formed by several breeds. The major contributing breeds were, Angus, Limousin, Charolais, and Simmental. The average contribution of these four breeds to the breed composition of animals having any fraction of the mentioned breeds were 0.46, 0.50, 0.50, and 0.50 for AN, CH, LI, and SM, respectively, for commercial cattle, and 0.51, 0.53, 0.59, and 0.41 for Rockwood cattle. With the primary use of purebred sires, commercial cattle were more representative of first generation crossbreds than Rockwood cattle. Rockwood and commercial cattle represented AI breeding as well as some herd bulls. Animals were slaughtered on the basis of a target commercial finishing end point of 8 mm of backfat.

The sources of DNA were frozen steaks stored in the Meat Science Laboratory at University of Guelph. The DNA was isolated from the meat sample by the standard phenol/chloroform method (Sambrook, et al. 1989; Hoelzel, 1992). The cell lysis buffer was modified as a 0.8 M concentration of urea, including 0.8 M Urea, 2% SDS, 100 mM Tris-HCI, 200 mM NaCl and 2 mM EDTA, pH 7.5.

Example 2

Primer Design and Sequencing of Amplified DNA Fragments

The primers 5'-CCTCGACTGCGTACCAATTCCGAAG-TAAAGCCAAAGGAACA-3'(SEQ ID NO: 2) (forward) and 5'-ATTTCTCTGATGGTGGCTGCTCACT-3'(SEQ ID NO: 3) (reverse) were designed based on a partial genomic DNA sequence of the bovine Calpastatin gene (Accession number AY008267) using the software Primer 3. The forward primer comprised a common tail 5'-CCTCGACTGCGTACCAAT-TCC-3'(SEQ ID NO: 4) as an approach to simplify the sequencing procedures when performing many reactions for different genes.

The PCR master mix was 6.71 µl $H_2O$, 1.0 µl 10×PCR buffer II, 0.73 µl 25 mM $MgCl_2$ solution, 0.6 µl 10 mM dNTPs Solution, 0.13 µl forward primer (20 pmol/µl), 0.13 µl reverse primer (20 pmol/µl), 0.1 µl AmpliTag Gold (5 U/µl) (Applied Biosystems, Foster City, Calif., USA) and 0.6 µl DNA template (50 ng/µl) in a 10 µl reaction solution. The PCR cycling condition were 95° C. for 10 mins. for 1 cycle, then 94° C. for 30 secs at. 69° C.; 62° C. for 30 secs.; and 72° C. for 30 secs. for 8 cycles; then 94° C. for 5 mins. for 1 cycle, and then maintained at 4° C. The PCR reactions were performed on the GenAmp PCR System 9700 (Applied Biosystems, Foster City, Calif., USA). The resulting PCR product was 532 bp in size. Sequencing of the PCR products revealed a G/C transversion in the products, resulting presence/absence of an Rsa I restriction site (recognizing sequence gt/ac) in the nucleotide position 257 bp. Sequencing was performed on the ABI PRISM 377 DNA sequencer (Applied Biosystems, Foster City, Calif., USA).

Example 3

PCR-RFLP Genotyping

Individual PCR-RFLP genotypes were distinguished for polymorphisms of the CAST gene at the nucleotide position corresponding to the nucleotide 232 of the sequence SEQ ID NO: 1. The PCR products were digested by Rsa I restriction endonuclease at 37° C. for 4 hrs in a 10 µl reaction solution including a 2.7 µl $H_2O$, 1.0 µl specific NEBuffer, 0.3 µl (3 units) restriction endonucleases, and 6 µl of a PCR product solution. DNA fragments from the digested PCR products were separated by 2.0% agarose gel containing ethidium bromide (0.4 µl /ml). Electrophoresis was performed in a 1×TBE buffer (10×concentrated stock solution: 108 gm Tris, 55 gm boric acid and 40 ml 0.5 M EDTA per liter, pH 8.0) containing ethidium bromide (3 µl of a 10 mg ethidium bromide/ml solution per 100 ml of gel solution) under 120V for about 45 min. The genotype for each individual was read under ultraviolet light, using Molecular Analyst Software (Bio-Rad Laboratories, Molecular Bioscience Group, Hercules, Calif.), as shown in FIG. 2.

Example 4

Phenotypic Information

Information on tenderness (shear force) of LM at 2 (SFL2), 7 (SFL7), 14 (SFL14), and 21 (SFL21) days postmortem and of semitendinosus muscle at 7 (SFS7) days postmortem, chemical fat (CF), grade fat (GFAT), quality grade (QG), LMA, percentage of lean (LEANYL), fat (FATYL) and bone (BONEYL) yield and hot carcass weight (HCW) were available on most of the 628 genotyped animals as shown in Table 1.

TABLE 1

Number of phenotypic records on the carcass and meat quality traits with corresponding means and SD

| Trait | Records | Mean | SD |
|---|---|---|---|
| FATYL, % | 602 | 25.4 | 5.25 |
| LEANYL, % | 602 | 55.1 | 4.70 |
| BONEYL, % | 602 | 19.5 | 2.00 |
| GFAT, mm | 623 | 9.9 | 3.91 |
| LMA, cm$^2$ | 601 | 86.5 | 13.72 |
| HCW, kg | 621 | 334.2 | 41.54 |
| SFL2, kg | 466 | 5.4 | 1.69 |
| SFL7, kg | 628 | 5.0 | 1.48 |
| SFL14, kg | 627 | 4.3 | 1.33 |
| SFL21, kg | 624 | 3.8 | 1.03 |

TABLE 1-continued

Number of phenotypic records on the carcass and meat quality traits with corresponding means and SD

| Trait | Records | Mean | SD |
|---|---|---|---|
| SFLavg, kg[z] | 465 | 4.5 | 1.03 |
| SFS7, kg | 620 | 5.0 | 0.97 |
| CF, % | 624 | 3.9 | 1.66 |
| QG A, %[y] | 75 | 12.2 | |
| QG AA, %[y] | 355 | 57.8 | |
| QG AAA, %[y] | 184 | 30.0 | |

[z]Average of all four shear force measurements of Longissimus muscle taken over 21-day postmortem period. (Shear force is the physical force applied on a cooked meat core sample necessary to shear the muscle fibers).
[y]Distribution of quality grades (A, AA, and AAA).

Warner Bratzler peak shear force measurements (kg) were used as an objective method of assessing tenderness (Shackleford et al. 1999). GFAT is the backfat thickness measurement taken at the 12$^{th}$ and 13$^{th}$ rib interface. LMA is the measure of the longissimus dorsi muscle area at the 12$^{th}$ and 13$^{th}$ rib interface using a tracing of the muscle. CF is the chemical analysis on a core meat sample that determines the percent intramuscular fat in the longissimus dorsi muscle. LEANYL, FATYL, and BONEYL were determined by dissection of a 4-bone rib section. Quality grade is the marbling grade used for grading in Canada with most carcasses falling in one of three grades (A, AA, AAA). Because only a few carcasses were classified as Prime, those animals were added to AAA carcasses for the analyses. A complete description of carcass measures available and methods used are described in Laborde et al. (2001) incorporated herein by reference in its entirety.

The genotypes of all animals were used to determine the allele frequencies. For the study of the association of the CAST SNP with carcass and meat quality traits, only animals with the required phenotypic information were used. The resulting number of records ranged from 466 for SFL2 to 624 for CF (Table 1).

Example 5

Analysis of the Association of the Single Nucleotide Polymorphism in the Calpastatin (CAST) Gene with Carcass and Meat Quality Traits in Beef Cattle The association of the genotypes for the SNP in the CAST gene with CF, GFAT, LMA, LEANYL, FATYL, BONEYL, and HCW was evaluated by genetic analysis using SAS PROC MIXED, fitting the following model, which included the known SNP genotypes (GG, GC, and CC) as fixed effects. $Y_{ijklm} = U + Gen_i + Sex_j + Slg_k + \beta_1 AN + \beta_2 LM + \beta_3 CH + \beta_4 SM + Sire_l + e_{ijklm}$ (1) where $Y_{ijklm}$ is the trait measured in the mth animal of j-th sex and k-th slaughter group; u is the overall mean for the trait; $Gen_i$ is the effect if the i-th genotype for the SNP in the CAST gene; $Sex_j$ is the fixed effect of the j-th sex (bull, heifer and steer); $Slg_k$ is the fixed effect of the k-th slaughter group (61 levels); $\beta 1$, $\beta 2$, $\beta 3$, $\beta 4$ are the regression coefficients on breed composition of Angus (AN), Limousin (LM), Charolais (CH) and Simmental (SM), respectively; $Sire_l$ is the random effect of the 1-th sire; and $e_{ijklm}$ is the residual random effect associated with the m-th animal.

Following the methods of Fernando et al. (1998), as genotypes were known, the mixed model equations of Henderson (1984) for model (1) were used in the analyses. Animals originated from 78 sires and all sires were known and assumed unrelated. The average size of the paternal half-sib families was 8.1.

The percentage of sires with less than 5, from 6 to 10, from 11 to 15 and more than 15 offspring were 42.3%, 23.1%, 25.6% and 9.0%, respectively. Slaughter groups were defined as animals from the same source (Commercial or Rockwood) and with the same slaughter date.

For analyzing the shear force measurements, CF was included as a linear covariate in the model (1) to account for possible effects of intramuscular fat on meat tenderness. Phenotypic and generic relationships between marbling and tenderness are not especially high, but show favorable direction (Bertrand et al. 2001), indicating that higher marbling is slightly associated with higher tenderness.

The repeated LM shear force measurements were analyzed individually within each postmortem period, as the average shear across postmortem periods and as repeated measures analysis. The effect of CAST SNP genotypes on quality grade was analyzed by chi-square analysis (PROC FREQ) and as a linear trait, applying model (1). In this case, scores of 1, 2 and 3 were assigned to quality grades A, AA and AAA, respectively.

Average allele substitution effects (Falconer and Mackay, 1996) were estimated and tested using model (1) replacing the classification effect of genotypes by a linear regression on number of C alleles (0, 1 or 2).

To keep reasonable probability values for Type I error, two levels of tests were performed. For initial assessment of the results, an overall value of $P<0.05(\alpha)$ was used. For a more detailed review of the results, a modified Bonferroni correction was used ($\alpha/\sqrt{n}$, Mantel, 1980) to account for the number of tests. The value of n was determined using a trait-wise approach, grouping traits according to type (Ye, 2003). Traits were grouped into two groups as follows: carcass yield traits (LEANYL, FATYL, GFAT, LMA and HCW) and meat quality traits (CF, QG, SFL2, SFL7, SFL14, SFL21, and SFS7). So, n was equal to 5 and 7 (BONEYL and SFLavg were linear functions of the other traits within their group) for carcass yield and meat quality traits, respectively, with the corresponding modified Bonferroni corrected significance levels of 0.022 and 0.019.

Example 6

Estimated Allele Frequency

The overall allele frequency was 63% for C and 37% for G. The overall observed genotypic frequencies (43.0%, 39.8% and 17.2% for CC, CG and GG, respectively) were not in agreement with Hardy-Weinberg equilibrium (P=0.001). The allelic frequency was different (P=0.001) between breeds (Angus, Limousin, Charolais, Simmental, and Others), with Simmental animals showing higher frequency of allele G (freq.=0.64) than all other breeds (freq. <0.38).

Example 7

Estimated Genotype Effects

Results of the association analyses (genotype analyses) are given in Table 2.

TABLE 2

Test for SNP genotype effects.

| Meat quality traits | P > F | Carcass traits | P > F |
|---|---|---|---|
| CF | 0.75 | HCW | 0.25 |
| QG (linear) | 0.70 | LMA | 0.12 |
| SFS7 | 0.14 | GFAT | 0.53 |
| SFLavg | 0.01 | LEANYL | 0.12 |
| QG (P > $\chi^2$) | 0.40 | FATYL | 0.04 |
|  |  | BONEYL | 0.04 |

CAST genotypes did not significantly influence CF (P=0.75), GFAT (P=0.53), HCW (P=0.25), and QG (P=0.40 by Chi-square test, and P=0.70 by F-test, treating QG as a linear trait).

Analysis of LM shear force at different individual aging times, as presented in Table 3, showed that CAST SNP genotypes had significant effect on SFL21 (P=0.007) and tended to affect SFL2 and SFL7 (P<0.08).

TABLE 3

CAST SNP genotype effect on peak shear force of Longissimus muscle (SFL) evaluated at 2, 7, 14 and 21 days postmortem and Semitendinous muscle (SFS) evaluated at 7 days postmortem

| Genotypes | SFL2 | SFL7 | SFL14 | SFL21 | SFLavg | SFS7 |
|---|---|---|---|---|---|---|
|  |  |  | Effect |  |  |  |
| CC | −0.51 | −0.38 | −0.21 | −0.20 | −0.38 | −0.10 |
| CG | −0.25 | −0.28 | −0.05 | −0.08 | −0.20 | 0.07 |
| GG | 0.00 | 0.00 | 0.00 | 0.00 | 0.00 | 0.00 |
|  |  |  | Least squares mean$^z$ |  |  |  |
| CC | 5.55a | 5.03a | 4.23a | 3.67a | 4.53a | 5.01a |
| CG | 5.81a | 5.13a | 4.39a | 3.95b | 4.71ab | 5.18a |
| GG | 6.06a | 5.41a | 4.44a | 3.87ab | 4.91b | 5.11a |
| P > F | 0.062 | 0.071 | 0.220 | 0.007# | 0.012# | 0.143 |
| Sex$^y$ | Ns$^x$ | Ns | Ns | Ns | Ns | Ns |
| Slgr | * | * | * | * | * | * |
| Breed | Ns | Ns | Ns | Ns | Ns | * |
| CF | Ns | * | * | * | Ns | Ns |

$^z$Means followed by different letters within a column are statistically different by Scheffé test (P < 0.015).
$^y$Other fixed effects included in the model: Sex = Gender (Bull, heifer and steer), Slgr = Slaughter group, Breed = Breed composition (covariate), CF = LM chemical fat (covariate).
$^x$Non significant (Ns) or significant (*) effect by F-test (P < 0.05).
Significant effect of genotypes after modified Bonferroni correction for trait-wise multiple tests at P = 0.05.

The CAST genotypes also significantly influenced (P=0.012) the average LM tenderness (SFLavg) over the 21-day aging period (Tables 2 and 3). Genotype CC had the most tender LM compared to genotypes CG and GG. The estimated difference between the effects of homozygote genotype CC and GG on SFLavg was −0.38 kg or 37% of the phenotype SD. The heterozygote genotype showed an intermediate tenderness. However, the difference between the homozygote genotypes CC and GG decreased from −0.51 kg to −0.20 kg from 2 to 21 days of aging. Those differences correspond to 30% to 19% of the phenotypic SD of the shear force measurements at 2 and 21 days, respectively. Table 4 presents results of the repeated measures analysis performed for LM shear force at different aging days.

TABLE 4

CAST genotype effect on Longissimus muscle shear force (repeated measures analysis)

| Genotype | Effect | Least squares mean |
|---|---|---|
| CC | −0.32 | 4.57a$^z$ |
| CG | −0.11 | 4.79ab |
| GG | 0.00 | 4.90b |
| P > F | 0.024 |  |
| Sex$^y$ | Ns$^x$ |  |
| Slgr | * |  |
| Breed | Ns |  |
| CF | * |  |

$^z$Means followed by different letters are statistically difference by Scheffé test (P < 0.025).
$^y$Other fixed effects included in the model: Sex = Gender (Bull, heifer and steer), Slgr = Slaughter group, Breed = Breed composition (covariate), CF = LM chemical fat (covariate).
$^x$Non significant (Ns) or significant (*) effect by F-test (P < 0.05).

The overall effect of genotype across aging days was significant (P<0.024), having the genotype CC −0.32 kg more tender LM than the genotype GG. The genotype CG had an intermediate tenderness. This result corroborates with the findings when the average tenderness over the 21-day postmortem period was analyzed, as shown in Table 3.

Figure 3:
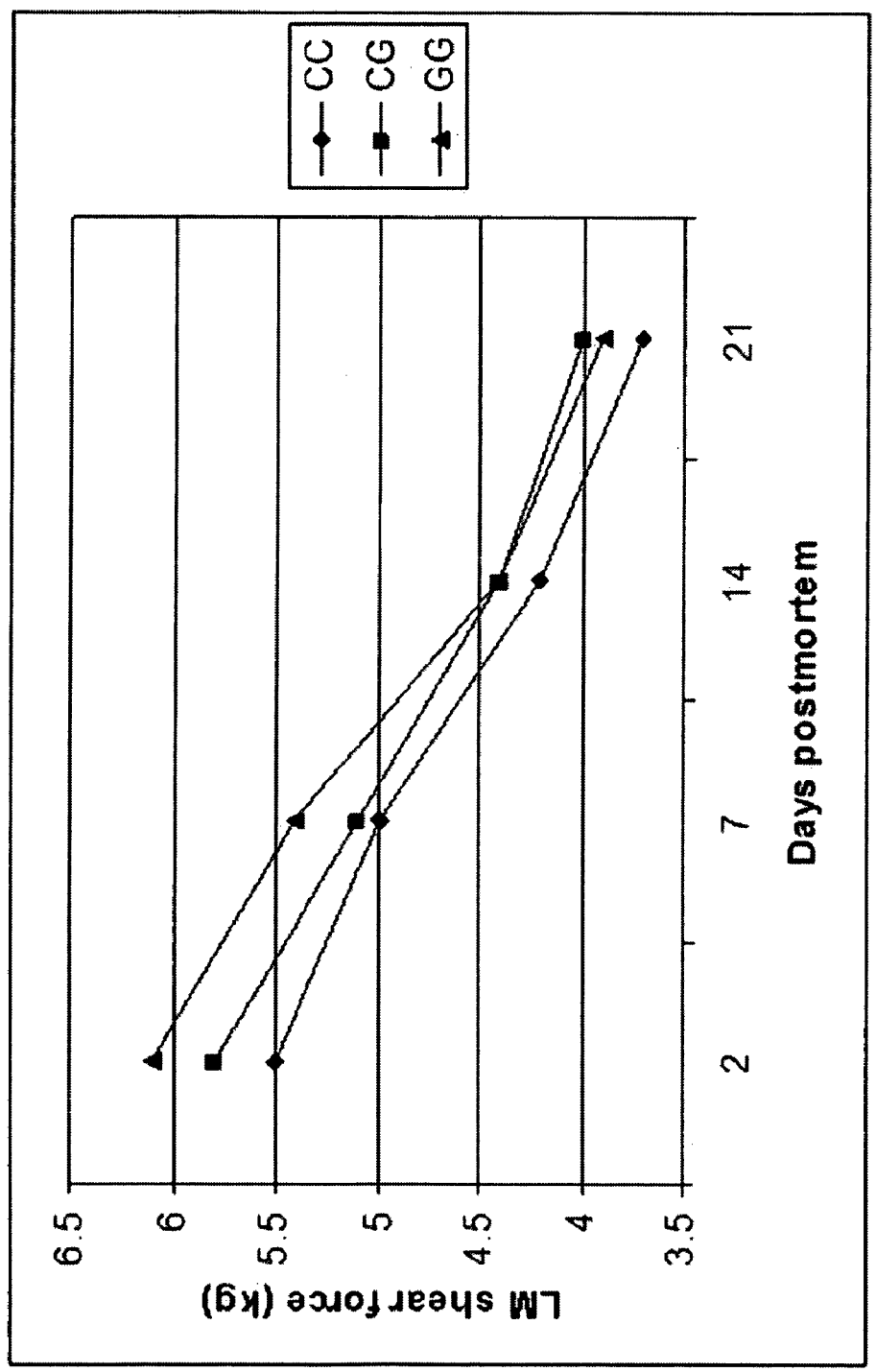
FIG. 3 illustrates the effect of CAST SNP genotypes on tenderness evaluation of Longissimus muscle (shear force) across post-mortem days 2-21.

FIG. 3 illustrates the effect of the genotypes on tenderness across postmortem days (from 2 to 21 days). The slopes of the linear regression of the shear force measures on the corresponding postmortem days for the three genotypes were not significantly different, indicating that the genotypes influenced the overall tenderness as shown in Tables 3 and 4, but not the rate of tenderization as the meat aged.

Figure 4:
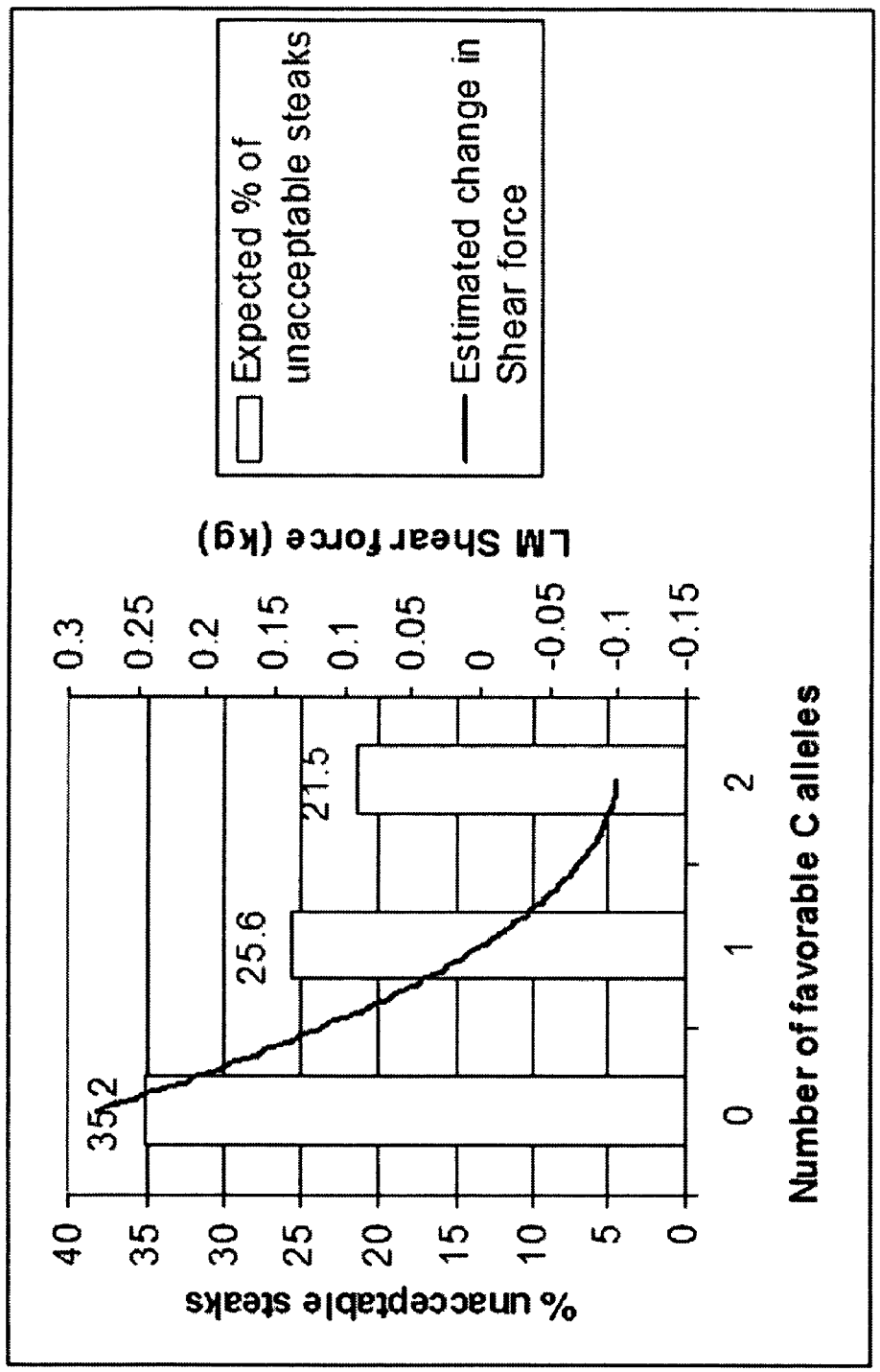
FIG. 4 illustrates the effect of the number of CAST SNP C alleles on tenderness evaluation of Longissimus muscle (shear force) at 7 days post-mortem and on the percentage of expected unacceptable Longissimus muscle steaks (shear force >5.7 kg).

FIG. 4 depicts the effect of number of C alleles on tenderness evaluation of Longissimus dorsi muscle at 7 days postmortem and on the percentage of expected unacceptable LM steaks (LM shear force >5.7 kg; Wheeler et al. 1997). The association of number of C alleles with percentage of unacceptable tough steaks was evaluated by Chi-Square after linear adjustment of shear force measurements to the same average level of chemical fat (3.9%). The estimated percentage of unacceptable steaks at 7 days postmortem was 35.2%, 25.6%, and 21.5% for cattle carrying 0, 1 and 2 copies of C allele, respectively (P=0.022). The corresponding change in shear force was 0.28 kg, 0.00kg, and −0.10 kg, respectively, setting the heterozygote genotype to zero.

In line with the effect on LM tenderness, CAST genotypes tended to affect SFS7 (P=0.14), with increased tenderness (−0.10 kg) in beef from genotype CC versus genotype GG.

Table 5 shows that CAST genotypes tended to influence LMA (P=0.12) and LEANYL (P=0.12) and significantly influenced FATYL (P=0.04) and BONEYL (P=0.04). The CC genotype tended to have smaller LMA (−1.77 cm$^2$) and lower lean yield (−1.21%) with higher fat yield (+1.67%) and lower bone yield (−0.47%) than GG genotype.

TABLE 5

CAST genotype effect on Longissimus muscle area (LMA), lean (LEANYL), fat (FATNYL) and bone (BONEYL) yield.

| Genotype | LMA | LEANYL | FATYL | BONEYL |
|---|---|---|---|---|
|  |  | Effect |  |  |
| CC | −1.77 | −1.21 | 1.67 | −0.47 |
| CG | −0.43 | −0.93 | 1.04 | −0.10 |

TABLE 5-continued

CAST genotype effect on Longissimus muscle area (LMA), lean (LEANYL), fat (FATNYL) and bone (BONEYL) yield.

| Genotype | Traits | | | |
|---|---|---|---|---|
| | LMA | LEANYL | FATYL | BONEYL |
| GG | 0.00 | 0.00 | 0.00 | 0.00 |
| | Least squares mean[z] | | | |
| CC | 90.0a | 56.1a | 24.5a | 19.4a |
| CG | 92.2a | 56.1a | 24.1ab | 19.8b |
| GG | 91.8a | 57.1a | 23.1b | 19.9b |
| P > F | 0.122 | 0.116 | 0.037 | 0.037 |
| Sex[y] | * | Ns[x] | Ns | * |
| Breed | * | * | * | * |
| Slgr | * | * | * | * |

[z]Means followed by different letters are statistically different by Scheffé test (P < 0.04).
[y]Other fixed effects included in the model: Sex = Gender (Bull, heifer and steer), Breed = Breed composition (covariate), Slgr = Slaughter group,
[x]Non significant (Ns) or significant (*) effect by F-test (P < 0.05).

Example 8

Allele Substitution Effect

The same model (1) was used to estimate the average allele substitution effect, replacing the fixed classification effect of genotype by a linear regression on the number of C alleles. The results are given in Tables 6 and 7.

TABLE 6

CAST SNP allele substitution effect ($\alpha$) on peak shear force of Longissimus muscle (SFL) evaluated at 2, 7, 14, and 21 days post mortem and Semitendinous muscle (SFS) evaluated at 7 days postmortem.

| | Trait | | | | | | |
|---|---|---|---|---|---|---|---|
| | SFL2 (kg) | SFL7 (kg) | SFL14 (kg) | SFL21 (kg) | SFLavg (kg) | SFLrep[z] (kg) | SFS7 (kg) |
| $\alpha$ | −0.255 | −0.171 | −0.116 | −0.133 | −0.189 | −0.167 | −0.072 |
| P > F | 0.018# | 0.032 | 0.097 | 0.025 | 0.003# | 0.008# | 0.216 |
| Sex[y] | Ns[x] | Ns | Ns | Ns | Ns | Ns | Ns |
| Slgr | * | * | * | * | * | * | * |
| Breed | Ns | Ns | Ns | Ns | Ns | Ns | Ns |
| CF | Ns | * | * | * | Ns | * | Ns |

[z]Shear force measures at different post-mortem days were analyzed by repeated measures analysis.
[y]Other fixed effects included in the model: Sex = Gender (Bull, heifer and steer), Slgr = Slaughter group, Breed = Breed composition (covariate), CF = LM chemical fat (covariate).
[x]Non significant (Ns) or significant (*) effect by F-test (P < 0.05).
Significant effect of genotypes after modified Bonferroni correction for trait-wise multiple tests at P = 0.05.

In general, no major changes were observed in relation to the genotype analyses. The effect of CAST SNP on tenderness was confirmed and it was even more evident within postmortem days through the allele substitution analyses, which assumes a linear effect of the alleles. The allele substitution effect was significant on FATYL and BONEYL and tended to affect LMA and LEANYL, which was also in agreement with the genotype analyses. The allele substitution analysis revealed a trend to affect HCW (P<0.12) with allele C decreasing HCW, which was observed with genotype analyses only at P<0.25.

TABLE 7

CAST SNP allele substitution effect ($\alpha$) on Longissimus muscle chemical fat (CF), grade fat (GFAT), quality grade (QG), Longissimus muscle area (LMA), hot carcass weight (HCW), and lean (LEANYL) fat (FATYL) and bone (BONEYL) yield.

| | Trait | | | | | | | |
|---|---|---|---|---|---|---|---|---|
| | CF (%) | GFAT (mm) | QG (1, 2, 3) | LMA (cm²) | HCW (kg) | LEANYL (%) | FATYL (%) | BONEYL (%) |
| $\alpha$ | −0.066 | −0.171 | −0.012 | −1.144 | −3.002 | −0.410 | 0.667 | −0.260 |
| P > F | 0.453 | 0.424 | 0.751 | 0.114 | 0.119 | 0.100 | 0.015# | 0.016# |
| Sex[z] | Ns[y] | Ns | Ns | * | * | Ns | Ns | * |
| Slgr | * | * | * | * | * | * | * | * |
| Breed | * | * | * | * | * | * | * | * |

[z]Other fixed effects included in the model: Sex = Gender (Bull, heifer and steer), Slgr = Slaughter group, Breed = Breed composition (covariate).
[y]Non significant (Ns) or significant (*) effect by F-test (P < 0.05).
Significant effect of genotypes after modified Bonferroni correction for trait-wise multiple tests at P = 0.05.

Similar results for genotype and allele substitution effects were obtained adjusting records for either the same average hot carcass weight or the same average grade fat thickness.

Therefore, Alleles of the CAST SNP identified in this study were segregating in the beef population with overall higher frequency for allele C than G. Allele C was associated with improvements in LM tenderness across post-mortem aging days, but tended to reduce LM area and lean yield, while increasing fat yield. Importantly for the beef industry, the difference in the tenderness is predicted to substantially reduce the percentage of carcasses rated unacceptably tough by consumers. It is expected that single and double C cattle would produce more tender carcasses and this would result in significantly fewer unsatisfactory eating experiences.

Example 9

Rsa I Restriction Digest Patterns of PCR Products Amplified Using Primers SEQ ID NOS: 2 and 3 and Genomic DNA Template from Homozygous and Heterozygous Animals with a Polymorphism Between Exons 5 and 6 of the CAST Locus (a) Not taking into account the 21 bp tag of primer SEQ ID NO: 2
GG homozygote: 257+266 bp
CC homozygote: 523 bp
GC heterozygote: 257+266+523 bp (b) Taking into account the 21 bp tag of primer SEQ ID NO: 2
GG homozygote: 12 bp+257 bp+275 bp
CC homozygote: 12 bp+532 bp
GC heterozygote: 12 bp+257 bp+275 bp+532 bp

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. An isolated nucleic acid molecule consisting of between 18 to 50 contiguous nucleotides of SEQ ID NO: 1 including position 282 of SEQ ID NO: 1, wherein said position 282 is a guanine.

2. An isolated nucleic acid molecule which consists essentially of SEQ ID NO: 2.

3. An isolated nucleic acid molecule which is SEQ ID NO: 2.

4. An isolated nucleic acid molecule which is SEQ ID NO: 3.

* * * * *

UNITED STATES PATENT AND TRADEMARK OFFICE
CERTIFICATE OF CORRECTION

PATENT NO. : 7,655,776 B2  Page 1 of 1
APPLICATION NO. : 11/183499
DATED : February 2, 2010
INVENTOR(S) : Schenkel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this

Twenty-eighth Day of December, 2010

David J. Kappos
*Director of the United States Patent and Trademark Office*